United States Patent [19]

Maurer et al.

[11] 4,442,839
[45] Apr. 17, 1984

[54] METHOD OF MODULATING ENERGY IN TRAIN OF ELECTRICAL PULSES

[75] Inventors: Donald D. Maurer; David E. Swift, both of Anoka; Zosim Ioffe, St. Paul, all of Minn.

[73] Assignee: EMPI, Inc., Fridley, Minn.

[21] Appl. No.: 257,737

[22] Filed: Apr. 27, 1981

[51] Int. Cl.³ ............................................. A61N 1/36
[52] U.S. Cl. ............................................... 128/419 R
[58] Field of Search ................ 328/109, 111, 115, 140, 328/173; 128/421; 307/546, 552, 553, 555, 264, 265; 331/175, 178, 179, 182, 183; 322/240

[56] References Cited

U.S. PATENT DOCUMENTS

| | | | |
|---|---|---|---|
| 2,808,826 | 10/1957 | Reiner et al. | 128/2.1 |
| 3,072,802 | 1/1963 | Myers et al. | 307/265 |
| 3,204,124 | 8/1965 | Durio, Jr. | 307/265 |
| 3,304,437 | 2/1967 | Dano | 307/265 |
| 3,318,158 | 5/1967 | Bromanber et al. | 328/173 |
| 3,392,289 | 7/1968 | Ehni | 307/264 |
| 3,646,940 | 3/1972 | Timm et al. | 128/421 |
| 3,817,254 | 6/1974 | Maurer | 128/421 |
| 3,888,261 | 6/1975 | Maurer | 128/420 |
| 4,014,347 | 3/1977 | Halleck et al. | 128/422 |
| 4,210,151 | 7/1980 | Keller, Jr. | 128/421 |
| 4,293,817 | 10/1981 | De Michele | 307/264 |

*Primary Examiner*—William E. Kamm
*Attorney, Agent, or Firm*—Burd, Bartz & Gutenkauf

[57] ABSTRACT

A transcutaneous electrical nerve stimulation apparatus having stimulus electrical pulses modulated in time and intensity to stimulate afferent nerves and cause the release of endogenous opiates which suppress pain. An astable pulse generator provides a first train of pulses at a selected repetition rate. A monostable pulse generator connected to receive the first train of pulses supplies a second pulse train having the frequency of the first train. The width of the pulses of the first train is varied over a predetermined range. A second monostable pulse generator connected to pulse amplifiers receives the first and second train of pulses and provides a supply pulse to the patient. Adjustable pulse modulators connected to the second pulse generators function to simultaneously increase the repetition rate of the first train of pulses and decrease the second train of pulses.

8 Claims, 4 Drawing Figures

METHOD OF MODULATING ENERGY IN TRAIN OF ELECTRICAL PULSES

TECHNICAL FIELD

This invention relates to the field of pulse generating circuits which generate a train of electrical pulses having coordinated pulse width, amplitude, and pulse rate for controlling the average energy output of the circuits.

BACKGROUND OF THE INVENTION

It is well known that pain can be alleviated by electrical pulses applied to the surface of the body or to electrodes implanted within the body. Initially, this electrical stimulation was applied in such a manner that the energy was only sufficient to stimulate sensory nerves, and effort was made to avoid stimulating muscle nerves which produce fasciculations. Subsequently it was found that electrical stimulation at sufficiently high levels to elicit muscle contractions resulted in greatly improved long term analgesia, but pain patients were in general unable to tolerate the unpleasant sensations which accompanied the high intensity stimulation.

To avoid this it has been proposed to stimulate muscle nerves with short trains of monophasic pulses, the pulse trains being at a low frequency. By this procedure, the current necessary to elicit muscle contraction can be reduced by one-third to one-half. Conventional transcutaneous electric nerve stimulation usually consists of a continuous train of pulses with three variable parameters. The rate may vary between 1 to 100 pulses per second, output between 0 to 70 milliampheres peak-to-peak, and pulse width between 0 to 400 micro-seconds. High rate transcutaneous electrical nerve stimulation usually refers to rates greater than 50 pulses per second. At these higher rates, if the interval is increased to a level which produces muscle contractions, few patients can tolerate the resulting sensations. By interrupting the pulse train periodically at a low rate, that is, by cycling the stimulation on and off, the sensations can be reduced to a degree, but generally patients cannot tolerate even interrupted pulses at the levels necessary for muscle stimulation.

SUMMARY OF THE INVENTION

The present invention is directed to a method of controlling the average energy in a train of electrical pulses by modulating the pulse rate range along with the modulation of the pulse rate, pulse width, and pulse amplitude. The method comprises the supplying of a train of electrical pulses and selectively increasing the repetition rate of the electrical pulses. When the repetition rate of the pulses is increased, there is an increase in output energy. The output energy is counteracted by simultaneously decreasing the width and amplitude of the electrical pulses to maintain the average energy in the train of electrical pulses within a selected energy range. When there is a decrease in the repetition rate of the electrical pulses, there is a decrease in the average energy. This is counteracted by simultaneously increasing the width and amplitude of the electrical pulses to maintain the average energy of the train of electrical pulses within the selected energy range.

According to a preferred embodiment of the method of the invention, the train of electrical pulses has a repetitive rate that is selectively increased and decreased. The average energy in the train is controlled by varying the width and amplitude of electrical pulses over a predetermined range simultaneously with an increase or decrease in the repetitive rate of the electrical pulses. The width and amplitude of the electrical pulses is increased when the repetitive rate of the electrical pulses is decreased and, inversely, when the width of the amplitude of the electrical pulses is decreased, the repetitive rate of the electrical pulses is increased. The limits of the range of the pulse width and amplitude are cyclically altered in conjunction with cyclically altering the repetitive rate of the electrical pulses between first and second values.

The method of the invention is embodied in a transcutaneous electrical nerve stimulation apparatus in which the stimulus pulses are modulated in both time and intensity in a prescribed manner, the pulse amplitude and width decreasing, while the pulse repetition rate increases, and vice versa. The result of this complex variation in the electrical stimulus is to produce a comfortable and pleasant sensation at levels sufficient to produce muscle contractions and stimulation of deep afferent nerves and so cause the release of endogenous opiates, such as endorphin, which suppress pain.

Various advantages and features of novelty which characterize the invention are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWINGS

In the drawings, in which like reference numerals indicate corresponding parts throughout the several views.

DESCRIPTION OF THE PREFERRED EMBODIMENT

Figure 1:
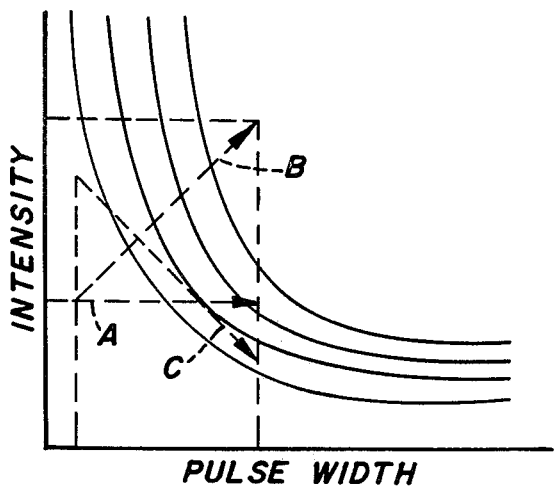
FIG. 1 is a diagram of strength-duration curves for various classes of nerve fibers.

FIG. 1 is a diagram of how strength-duration curves would appear for a different class of nerves if all were plotted on the same coordinates. Here stimulus intensity increases along the vertical axis and pulse width increases along the horizontal axis. Curve A shows the path of modulation in which the pulse width is varied, the amplitude remaining constant. Curve B shows the path of modulation in which amplitude increases with pulse width, and has been preferred modulation to maximize the recruitment with time of various classes of nerves, thereby increasing sensory input to the biological system. Curve C shows the path of modulation in which amplitude decreases with pulse width.

Figure 2:
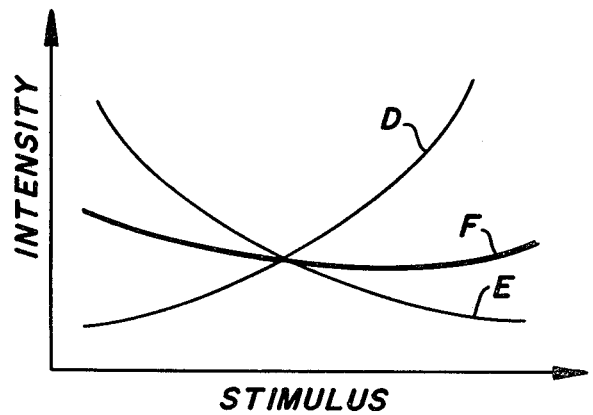
FIG. 2 shows the relation between the pulse modulations of FIG. 1 and the subjective perception of intensity by the patient.

Turning now to FIG. 2, the curves are plotted which show the variation of the perception or subjective awareness of stimulation intensity on the vertical axis with rate decrease and pulse amplitude and pulse width on the horizontal axis increase. Curve D corresponds to Curve B of FIG. 1, and shows that as the pulse amplitude and pulse width increase, the intensity perceived by the patient also increases. Curve E shows that if the pulse rate changes, amplitude and pulse width remaining the same, the patient perceives a decrease in stimulus intensity. Curve F shows that when the rate decreases, as intensity and pulse width increase, no great change in stimulus is sensed by the patient.

Figure 3:
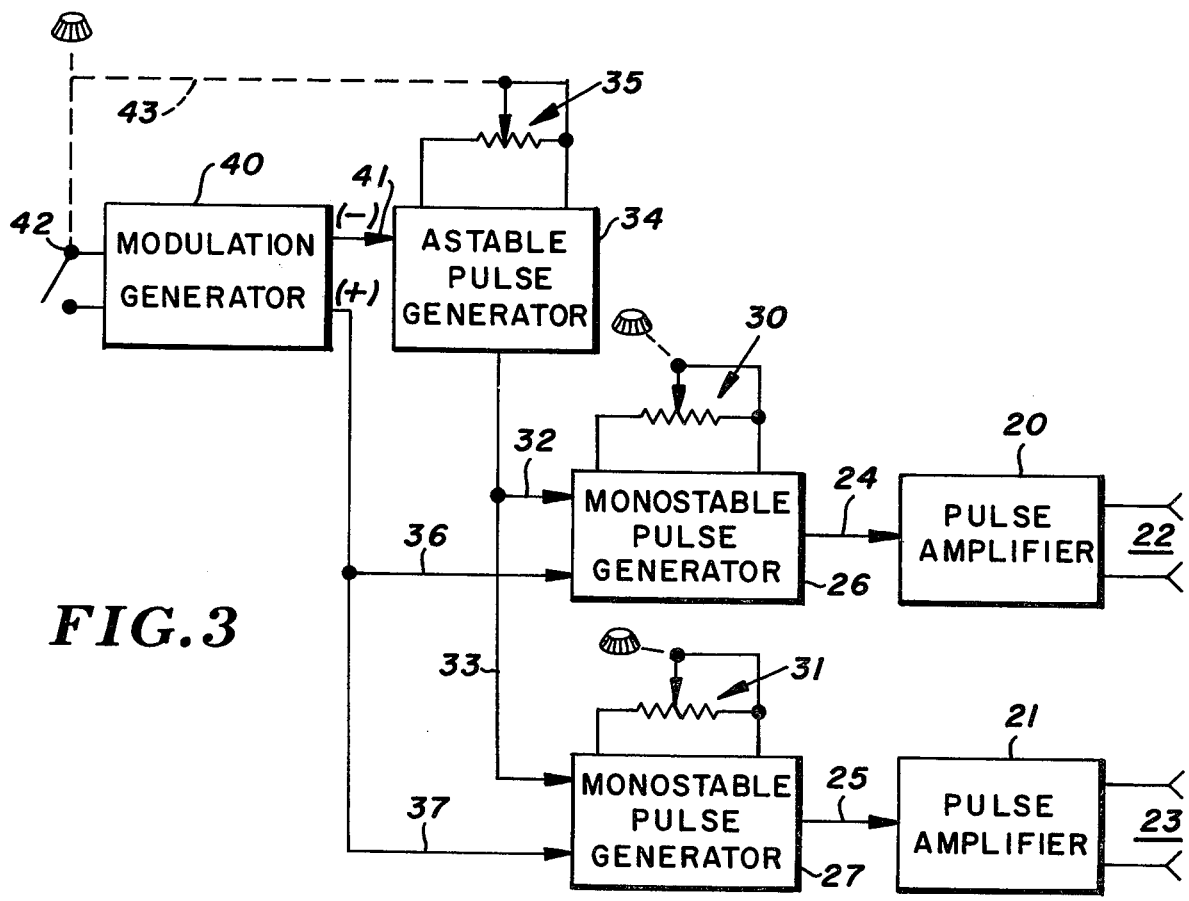
FIG. 3 is a block diagram of electrical stimulation apparatus according to the invention.

The present invention provides stimuli having variations in the pulse amplitude, pulse width, and pulse rate necessary to accomplish the result of Curve F. As shown in FIG. 3, a pair of patient treatment units 20 and 21 are shown as energizing pairs of electrodes 22 and 23. Each unit comprises a pulse amplifier and pulse-width-to-amplitude converter. The units are energized through conductors 24 and 25 from monostable pulse generators 26 and 27, respectively, having individual manual amplitude controls 30 and 31 for adjustment by the patient. Generators 26 and 27 are triggered through conductors 32 and 33 from an astable pulse generator 34 having a manual rate control 35 for adjustment by the patient. Generators 26 and 27 are controlled through conductors 36 and 37 by a modulation pulse generator and control 40, which also controls generator 34 through a conductor 41. Latching of control 40 is accomplished by a switch 42 actuated with control 35 by a mechanical connection 43.

Figure 4:
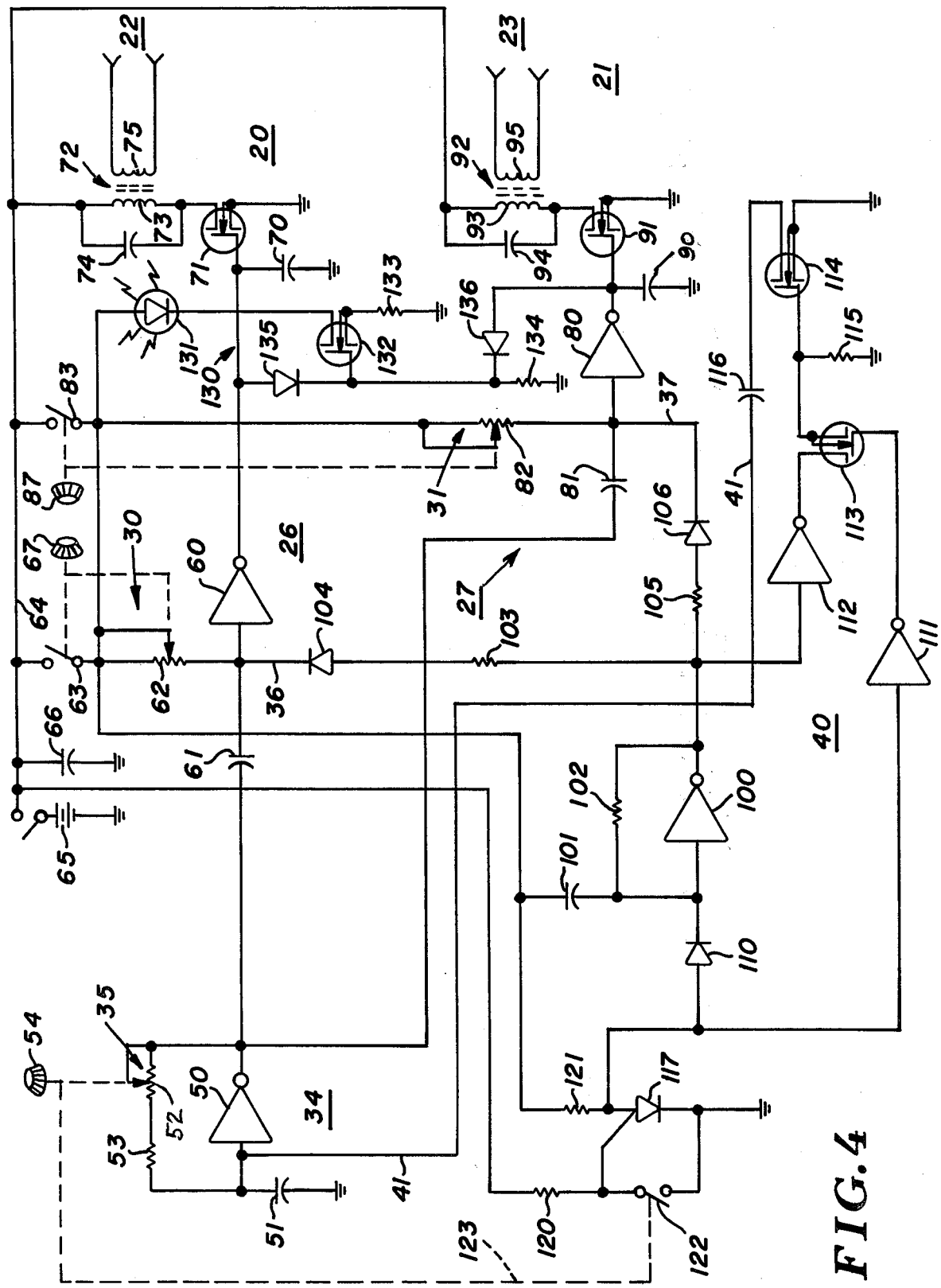
FIG. 4 is a circuit diagram of the device of FIG. 2.

Turning now to FIG. 4, astable pulse generator 34 is shown to comprise an inverter 50, a capacitor 51, and feed back resistors 52 and 53, the former being variable by an adjusting knob 54 and comprising manual adjustment 35 of FIG. 4.

Monostable pulse generator 26 is shown to comprise an inverter 60, a capacitor 61, and a variable resistor 62 connected through a switch 63 to a positive bus 64 energized from the positive terminal of a battery 65 having its negative terminal grounded. A filter capacitor 66 is provided. Switch 63 and resistor 62 are actuated by a common knob 67 and constitute adjustment 30 of FIG. 3.

Pulse amplifier 20 comprises a capacitor 70, a MOSFET (field effect transistor) 71, and a transformer 72 having a primary winding 73 shunted by a capacitor 74 and connected to bus 64, and a secondary winding 75 connected to electrodes 22.

Monostable pulse generator 27 is shown to comprise an inverter 80, a capacitor 81, and a variable resistor 82 connected through a switch 83 to positive bus 64. Switch 83 and resistor 82 are actuated by a common knob 87 and constitute adjuster 31 of FIG. 3.

Pulse amplifier 21 comprises a capacitor 90, a MOSFET 91, and a transformer 92 having a primary winding 93 shunted by a capacitor 94 and connected to bus 64, and a secondary winding 95 connected to electrodes 23.

Modulation generator 40 comprises an inverter 100, a capacitor 101 connected to bus 64 through switches 63 and 83 in parallel, and a feed back resistor 102. It is connected to generator 26 through a resistor 103, a diode 104, and conductor 36, and to generator 27 through a resistor 105, a diode 106, and conductor 37. Modulation generator 40 also comprises a diode 110, a pair of inverters 111 and 112, a pair of MOSFETS 113 and 114, a coupling resistor 115, a coupling capacitor 116, and a programmable unijunction transistor 117 powered through a pair of resistors 120 and 121. A modulation mode selector switch 122 is associated with transistor 117, and is actuated with knob 54 by a mechanical connection 123 as a part of manual adjustment 35.

A visual monitoring circuit 130 is shown to comprise a light emitting diode 131 energized from battery 65 through switches 63 and 83 in parallel under the control of a MOSFET 132 and a current limiting resistor 133. Input circuitry for MOSFET 132 has a common resistor 134 and includes a diode 135 connected to inverter 60 and a diode 136 connected to inverter 80.

In use, switch 122 is closed to inhibit modulation as will be described below, the circuit is energized to provide continuous stimulation to assist in placing one or both pairs of electrodes 22 and 23 on the patient's body in optimum positions, one or both of switches 63 and 83 being closed for this purpose, and monitoring circuit 130 giving indication of correct operation of the stimulator. After the electrodes are positioned, switch 122 is opened and the character of the stimuli is adjusted at will by operating controls 30, 31, and 35.

Inverter 50 with capacitor 51 and resistors 52 and 53 comprises astable pulse generator 34 and sets the basic pulse rate by the setting of resistor 52. The output pulses from generator 34 are supplied to capacitor 61 of monostable pulse generator 26 and capacitor 81 of monostable pulse generator 27, which supply trains of pulses of MOSFET 71 of patient unit 20 and MOSFET 91 of patient unit 21, the pulses being variable in width and amplitude in the same sense by adjusting controls 62 and 82, respectively.

Inverter 100 with capacitor 101 and resistor 102 comprises a second astable pulse generator for setting the basic rate of change of modulation for the stimulator. Transistor 117 is switched to latch in the modulation mode via diode 110, once it is selected by switch 122. When the switch is momentarily actuated, transistor 117 turns on and latches until power is removed, reverse biasing diode 110 and allowing capacitor 101 to charge. This is periodically switched by inverter 100 to produce a second train of pulses which are communicated through resistor 103 and diode 104 to inverter 60, and through resistor 105 and diode 106 to inverter 80.

When the output pulse of inverter 100 is at a high level, resistor 103 is in effect placed in parallel with resistor 62. The reduced resistance of the parallel combination causes capacitor 61 to charge more rapidly, resulting in switching of inverter 60 sooner so that the width of the pulses from inverter 60 is reduced. When the output of the inverter 100 is at a low level, diode 104 is reverse biased, since its anode is now at ground and its cathode is at supply voltage through resistor 62. This results in the output pulses of inverter 60 increasing in width to a preset value determined by the setting of resistor 62. Thus, as inverter 100 switches between high and low outputs, the pulse width alternates between wider and narrower.

This variation in pulse width is amplified by transistor 71 and transformer 72. The parameters of transformer 72 are such that as the output pulse width varies from wide to narrow, the output pulse amplitude varies from high to low, so that the stimulus to the patient fluctuates periodically in intensity and pulse width.

An action similar to that just described for inverter 60 also occurs for inverter 80 and affects the output of patient unit 21.

A second sequence of events occurs to vary the pulse rate of generator 34. When the output of inverter 100 goes to a high level, the signal is conveyed to inverter 112 whose output goes to a low level. If transistor 113 is turned on, which is the case when transistor 117 is on and a low signal is supplied to inverter 111, then the output pulse of inverter 112 can be communicated through transistor 113 to turn transistor 114 off.

When inverter 100 goes to a low level, inverter 112 has a low input and a high output. Transistor 113 is on transmitting the high level to transistor 114 to turn it on, thus connecting capacitor 116 in parallel with capacitor 51 of generator 34 and suddenly lowering the rate of pulses from inverter 50. When inverter 100 returns to a high level, capacitor 116 is disconnected from inverter 50 which resumes its former rate of pulses. As pointed out above, when the output of inverter 100 is high, the pulse width is decreased and the amplitude is reduced. This occurs simultaneously with the increase in the pulse repetition rate.

In one embodiment of the invention the output voltage varied between 0 and 60 volts, the pulse width range was 0 to 400 micro-seconds, the pulsing rate was from 1 to 100 pulses per second, the modulation rate was 1 cycle per second, and the changes during modulation were 0 to 40 percent amplitude, 0 to 60% pulse width, and 10 to 40% pulse rate change.

From the above it will be evident that the invention comprises a stimulator in which pulse repetition rate varies between two levels, the variation being accompanied by changes in the pulse width and amplitude, so that an increase in the average pulse energy due to increase in repetition rate is counteracted by a simultaneous decrease due to individual pulses being reduced in width and amplitude.

Numerous characteristics and advantages of the invention have been set forth in the foregoing description, together with details and structure of the function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

The embodiments of the invention in which an exclusive property or privilege is claimed are defined as follows:

1. A method of controlling the average energy in a train of electrical pulses comprising: supplying a train of electrical pulses, selectively increasing and decreasing the repetition rate of said electrical pulses, counteracting the energy increase associated with an increase in repetition rate of the electrical pulses by simultaneously decreasing the width and amplitude of the electrical pulses and modulating the pulse rate range to reduce the average energy in said train of electrical pulses, and counteracting the energy decrease associated with a decrease in repetition rate of the electrical pulses by simultaneously modulating the pulse rate range and increasing the width and amplitude of the electrical pulses.

2. The method of claim 1 including: manually adjusting the rate range of the train of electrical pulses.

3. The method of claim 1 including: cyclically alternating the pulse repetition rate between higher and lower values and simultaneously altering the width and amplitude of the electrical pulses between the lower and higher values.

4. The method of claim 1 wherein: the pulse repetition rate change is between 0 and about 40% and the pulse width change is between 0° and 60°.

5. A method of controlling the average energy in a train of electrical pulses comprising: supplying a train of electrical pulses at a repetitive rate, selectively increasing and decreasing the repetitive rate of said electrical pulses, varying the pulse rate range, pulse width and pulse amplitude of said electrical pulses over a predetermined range simultaneously with an increase or decrease in the repetitive rate of said electrical pulses, said width and amplitude of said electrical pulses being decreased when the repetitive rate of said electrical pulses is increased and said width and amplitude of said electrical pulses being increased when the repetitive rate of said electrical pulses is decreased, and cyclically altering the limits of said range of pulse widths and amplitudes, and cyclically altering the repetitive rate of said electrical pulses between first and second values.

6. The method of claim 5 wherein: the train of electrical pulses is supplied at a manually adjustable rate range.

7. The method of claim 5 including: cyclically alternating pulse repetition rate between higher and lower values and simultaneously altering the pulse width and amplitude between lower and higher values.

8. The method of claim 5 wherein: the pulse repetition rate changes between 0 and about 40% and the pulse width changes between 0 and 60%.

* * * * *